United States Patent
Rajan et al.

(10) Patent No.: US 8,805,500 B2
(45) Date of Patent: Aug. 12, 2014

(54) ATRIAL NERVE STIMULATION WITH VENTRICULAR PACING

(75) Inventors: Vinayakrishnan Rajan, Maastricht (NL); Richard N. M. Cornelussen, Maastricht (NL); Berthold Stegemann, Aachen (DE); Lilian Kornet, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 446 days.

(21) Appl. No.: 13/047,958

(22) Filed: Mar. 15, 2011

(65) Prior Publication Data

US 2012/0239100 A1    Sep. 20, 2012

(51) Int. Cl.
 *A61N 1/00*    (2006.01)
(52) U.S. Cl.
 USPC ............................... 607/9; 607/17
(58) Field of Classification Search
 USPC ...................................... 607/9, 17
 See application file for complete search history.

(56) References Cited

U.S. PATENT DOCUMENTS

| | | | |
|---|---|---|---|
| 5,213,098 A | 5/1993 | Bennett et al. |
| 5,507,784 A | 4/1996 | Mehra et al. |
| 6,006,134 A | 12/1999 | Hill |
| 6,122,545 A | 9/2000 | Struble |
| 6,266,564 B1 | 7/2001 | Hill et al. |
| 6,285,907 B1 | 9/2001 | Kramer et al. |
| 6,738,667 B2 | 5/2004 | Deno |
| 6,934,586 B2 | 8/2005 | Struble |
| 7,096,064 B2 | 8/2006 | Deno |
| 7,103,403 B1 | 9/2006 | Bradley |
| 7,139,607 B1 | 11/2006 | Shelchuk |
| 7,206,634 B2 | 4/2007 | Ding |
| 7,233,824 B2 | 6/2007 | Kleckner |
| 7,269,457 B2 | 9/2007 | Shafer |
| 7,389,141 B2 | 6/2008 | Hall |
| 2003/0050670 A1 | 3/2003 | Spinelli et al. |
| 2004/0010291 A1 | 1/2004 | Wagner et al. |
| 2005/0102002 A1 | 5/2005 | Salo et al. |

(Continued)

FOREIGN PATENT DOCUMENTS

| | | |
|---|---|---|
| EP | 474958 A2 | 3/1992 |
| EP | 1 234 597 A2 | 8/2002 |

(Continued)

OTHER PUBLICATIONS (PCT/US2012/022026) PCT Notification of Transmittal of the International Search Report and the Written Opinion of the International Searching Authority.

(Continued)

*Primary Examiner* — Nicole F Lavert
(74) *Attorney, Agent, or Firm* — Michael C. Soldner

(57) ABSTRACT

A method and medical device for delivering an atrial pacing pulse to an atrial chamber to generate an evoked atrial depolarization, delivering a stimulation pulse to an atrioventricular node during a stimulation window to increase a PR interval of the heart, the stimulation window having a start time corresponding to the delivered atrial pacing pulse so that the stimulation pulse is delivered during a refractory period corresponding to the evoked atrial depolarization, and delivering a ventricular pacing pulse to a first ventricular chamber during the increased PR interval to cause a contraction of the first ventricular chamber to occur prior to a contraction of a second ventricular chamber to increase dyssynchrony between the contraction of the first ventricular chamber and the contraction of the second ventricular chamber.

20 Claims, 6 Drawing Sheets

(56) References Cited

U.S. PATENT DOCUMENTS

| | | | |
|---|---|---|---|
| 2007/0203522 A1 | 8/2007 | Hettrick et al. | |
| 2008/0114407 A1 | 5/2008 | Pastore | |
| 2008/0140146 A1* | 6/2008 | Garner et al. ............ | 607/27 |
| 2008/0195174 A1 | 8/2008 | Walker et al. | |
| 2009/0005845 A1 | 1/2009 | David | |
| 2009/0192560 A1 | 7/2009 | Arcot-Krishnamurthy et al. | |
| 2009/0318986 A1 | 12/2009 | Alo et al. | |
| 2010/0069990 A1 | 3/2010 | Muller | |

FOREIGN PATENT DOCUMENTS

| | | |
|---|---|---|
| WO | 2006074164 A1 | 7/2006 |
| WO | 2007/115188 A2 | 10/2007 |
| WO | 2007115188 A2 | 10/2007 |
| WO | 2008/027242 A2 | 3/2008 |
| WO | 2008/109040 A2 | 9/2008 |
| WO | 2011/000558 A1 | 1/2011 |

OTHER PUBLICATIONS (PCT/US2012/022019) PCT Notification of Transmittal of the International Search Report and the Written Opinion of the International Searching Authority.

Laurent, G. et al.; "Left atrio-ventricular resynchronisation pacing therapy may improve diastolic heart failure symptoms"; European Heart Journal; vol. 31, Supplement 1; Sep. 2, 2010; p. 730.

Frenneaux M., et al., "Ventricular-arterial and ventricular-ventricular interactions and their relevance to diastolic filling" Prog. Cardiovas. Dis. 2007 Jan.-Feb., pp. 252-262, vol. 49(4).

Carlson MD, et al. "Selective stimulation of parasympathetic nerve fibers to the human sinoatrial node" Circulation. Apr. 1992, pp. 1311-1317. vol. 85(4).

Bleasdale RA, et al. "Left ventricular pacing minimizes diastolic ventricular interaction, allowing improved preload-dependent systolic performance" Circulation. Oct. 2004,, pp. 2395-2400, vol. 110(16).

* cited by examiner

US 8,805,500 B2

ATRIAL NERVE STIMULATION WITH VENTRICULAR PACING

TECHNICAL FIELD

The instant disclosure relates generally to implantable medical devices and, in particular, to a cardiac stimulation method and apparatus for atrial nerve stimulation with ventricular pacing.

BACKGROUND

Diastolic heart failure (DHF) is a form of heart failure that occurs when ventricular filling is impaired during the diastolic phase of the cardiac cycle. An estimated fifty percent or more of all heart failure patients may suffer from diastolic heart failure. Patients with DHF may experience symptoms related to congestive heart failure, including reduced exercise capacity and impaired quality of life. Impaired ventricular filling can be caused by ventricular hypertrophy, which increases the stiffness of the ventricular chamber. Ejection fraction may be preserved in patients with diastolic heart failure, which is sometimes referred to as heart failure with preserved ejection fraction or HFpEF. Patients suffering from systolic heart failure typically experience a worsening ejection fraction as the heart muscle becomes less effective at pumping or ejecting blood. Patients suffering from systolic heart failure may have impaired diastolic function as well.

Cardiac resynchronization therapy (CRT) is a cardiac stimulation therapy administered to patients having systolic HF. Impaired ejection during cardiac systole can be caused by dyssynchrony of the right and left ventricular chambers. When proper ventricular synchrony is restored, by pacing either one or both ventricular chambers, an improvement in ejection fraction is possible. A need remains, however, for treating impaired diastolic filling in patients experiencing DHF.

DETAILED DESCRIPTION

In the following description, references are made to illustrative embodiments. It is understood that other embodiments may be utilized without departing from the scope of the disclosure.

Impaired filling of the left ventricle in DHF can be due to hypertrophy of the left ventricular chamber resulting in decreased compliance of the chamber and consequently reduced filling of the chamber during cardiac diastole. Competition between the right and left ventricle for the pericardial volume during the filling phase can exacerbate the impaired filling of the left ventricle (LV). If the right and left ventricles are contracting and relaxing in a substantially synchronous manner, the reduced compliance of the LV will cause the LV to fill more slowly than the right ventricle (RV). Because the LV and RV are enclosed within the limited volume of the pericardial sac, faster filling of the RV reduces the volume available for the LV to continue filling during ventricular diastole. The ejection fraction of the LV may be preserved but the total end-diastolic and end-systolic volumes will be reduced, potentially resulting in pulmonary congestion, edema, and a reduction in cardiac output.

To address this "competition" between the RV and LV for the available pericardial volume during diastolic filling, a cardiac stimulation therapy for increasing the dyssynchrony between the RV and LV is described herein for improving LV filling as a treatment option for patient's suffering from DHF.

Figure 1:
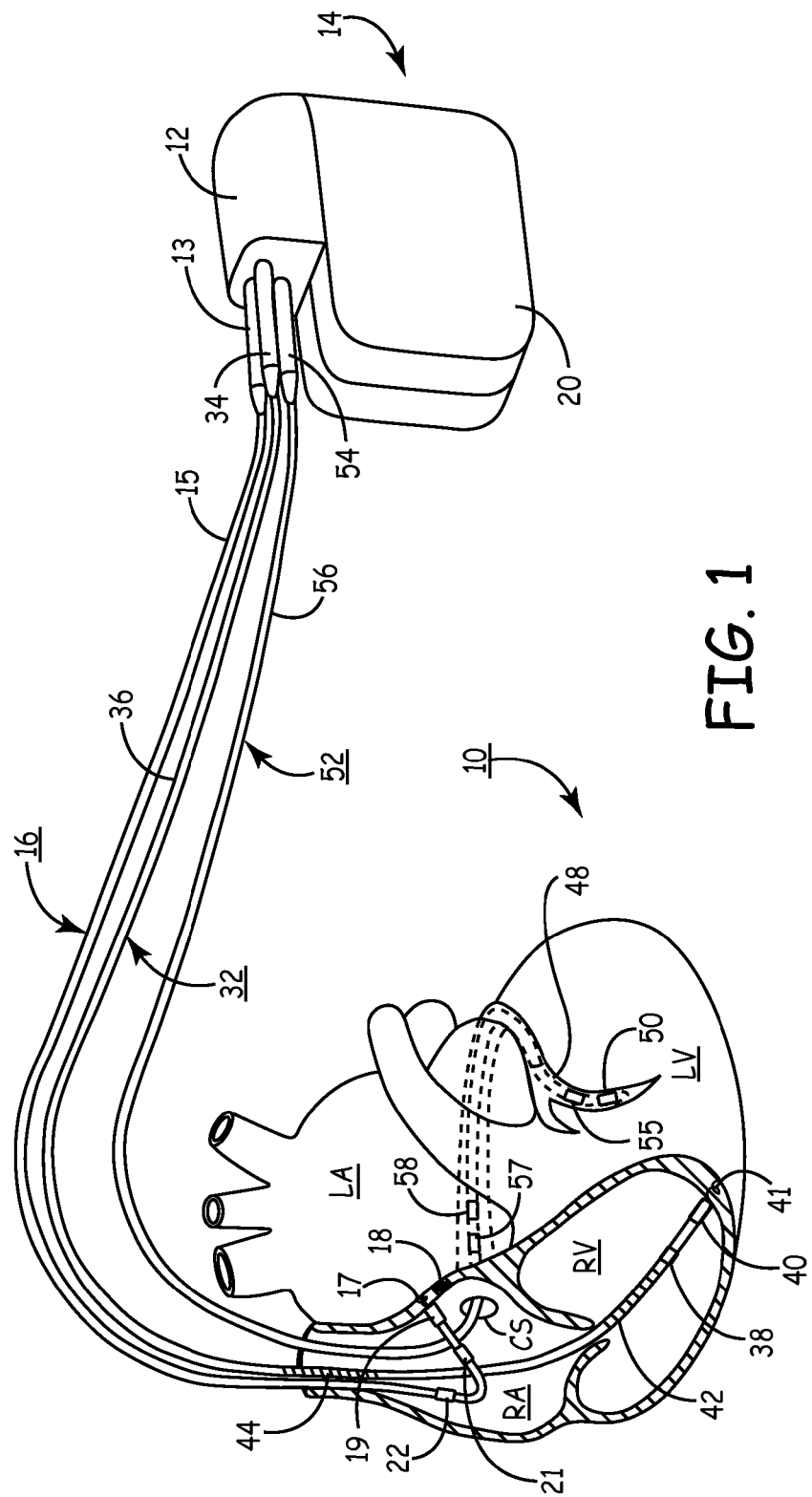
FIG. 1 is a schematic diagram of an implantable medical device (IMD) according to one embodiment for delivering a cardiac stimulation therapy to a HF patient.

In FIG. 1, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the great cardiac vein that extends further inferiorly into cardiac vein branches.

A cardiac cycle normally commences with the generation of a depolarization impulse in the sinoatrial node (SA node, not shown) in the right atrial wall. The impulse then conducts through the right atrium, to the left atrial septum and reaches the atrioventricular node (AV node) 18 within about 40 ms and the furthest walls of the RA and LA within about 70 ms. Approximately 50 ms following electrical activation, the atria contract. The aggregate RA and LA depolarization wave appears as the P-wave of the PQRST complex when sensed across external ECG electrodes and displayed. The component of the atrial depolarization wave passing a pair of unipolar or bipolar pace/sense electrodes, respectively, located on or adjacent the RA or LA is also referred to as a sensed P-wave.

The depolarization impulse that reaches the AV node conducts down the bundle of His in the intra-ventricular septum after a delay of about 120 ms. This delay between atrial depolarization and ventricular depolarization allows time for the atrial contraction to contribute to ventricular filling during diastole. The depolarization wave reaches the apical region of the heart about 20 ms later and then travels superiorly though the Purkinje fiber network over the remaining 40 ms. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. When the amplitude of the QRS ventricular depolarization wave passing a bipolar or unipolar pace/sense electrode pair located on or adjacent to the RV or LV exceeds a defined threshold amplitude, it is sensed as an R-wave.

The IMD 14 in FIG. 1 is configured according to one embodiment for delivering a cardiac stimulation therapy. Three transvenous leads 16, 32 and 52 connect the IMD 14 with the patient's heart 10. Each lead has at least one electrical conductor and pace/sense electrode, and a remote indifferent can electrode (IND_CAN) 20 is formed as part of the outer surface of the housing of the IMD 14. The pace/sense electrodes and the remote indifferent can electrode 20 can be selectively employed to provide a number of unipolar and bipolar pace/sense electrode combinations for pacing and sensing functions. The depicted positions in or about the right and left heart chambers are illustrative. Moreover other leads and pace/sense electrodes may be used instead of the depicted leads and pace/sense electrodes that are adapted to be placed at electrode sites on or in operative relation to the RA, LA, RV and LV as long as electrical stimulation of the AV node parasympathetic nerves and at least one ventricle can be achieved.

The depicted transvenous, endocardial RA lead 16 is passed through a vein into the RA chamber of the heart 10, and the distal end of the RA lead 16 is attached to the RA wall by a tip electrode 17. Tip electrode 17 is positioned in, on or near the interatrial septum, in the vicinity of the AV node 18, shown schematically. The AV node 18 is located along the interatrial septum close to the tricuspid valve. In the context of the illustrated embodiment, the distal end of the lead 16 is located near the AV node 18 so that tip electrode 17 and ring electrode 19 form a bipolar electrode pair operatively positioned to stimulate the parasympathetic nerves innervating the AV node. In some embodiments, the specialized AV nodal tissue may be stimulated directly. As such, the terms "AV nodal stimulation" or "AV node stimulation" inclusively refer to stimulation of the parasympathetic nerves of the AV node or direct stimulation of the AV nodal tissue.

In other embodiments, lead 16 may be advanced into the pulmonary artery to achieve stimulation of the parasympathetic nerves of the AV node. In still other embodiments, an epicardial lead positioned over the AV nodal fat pad may be used for delivering stimulation to the parasympathetic nerves innervating the AV node.

The endocardial RA lead 16 is shown to include a second pair of electrodes 21 and 22 that may be used for delivering RA pacing pulses to the atrial myocardium. Any of the RA lead electrodes 17, 19, 21 and 22 may be used in a bipolar combination for sensing atrial P-waves for use in timing stimulation of the AV node nerves during an atrial refractory period. Alternatively any of electrodes 17, 19, 21 and 22 may be used in a unipolar configuration with indifferent can electrode 20 for sensing and/or pacing the RA. RA lead 16 is formed with an in-line connector 13 fitting into a bore of IMD connector block 12. In-line connector 13 is coupled to electrically insulated conductors within lead body 15 and connected with electrodes 17, 19, 21 and 22.

Transvenous RV lead 32 is passed through the RA chamber of the heart 10 and into the RV where its distal ring and tip RV pace/sense electrodes 38 and 41 are positioned in the RV apex. Tip electrode may be a retractable helix electrode extending from distal lead end 40. The RV lead 32 is formed with a connector 34 fitting into a bore of IMD connector block 12 that is coupled to electrically insulated conductors within lead body 36 and connected with distal tip RV pace/sense electrode 41 and proximal ring RV pace/sense electrode 38. Electrodes 41 and 38 may be used in a bipolar configuration for pacing and/or sensing in the RV. Alternatively, a unipolar RV lead could be substituted for the depicted bipolar RV lead 32 and be employed with the IND_CAN electrode 20, or one of the distal tip RV pace/sense electrode 41 or proximal ring RV pace/sense electrode 38 can be employed with the IND_CAN electrode 20 for unipolar pacing and/or sensing.

RV lead 32 further includes an RV coil electrode 42 and a superior vena cava (SVC) coil electrode 44 which are coupled to respective insulated conductors extending within lead body 36 to connector 34 engaged in a bore of IMD connector block 12. The coil electrodes 42 and 44 are electrically coupled to high voltage circuitry within IMD 14 for delivering high voltage cardioversion/defibrillation (CV/DF) shocks to heart 10.

In this illustrative embodiment, a transvenous LV CS lead 52 is passed through the RA chamber of the heart 10, into the ostium of the coronary sinus and then inferiorly in a branching vessel of the great cardiac vein 48 to extend a pair of distal LV CS pace/sense electrodes 50 and 55 alongside the LV chamber. The LV CS lead may employ a deployable fixation mechanism or may instead rely on the close confinement within the cardiac vein to maintain the pace/sense electrodes 50, 55 at a desired site. The LV CS lead 52 is coupled to internal IMD circuitry via proximal end connector 54 fitting into a bore of IMD connector block 12.

The distal, LV CS pace/sense electrodes 50 and 55 may be paired in a bipolar combination for delivering LV pace pulses across the bulk of the left ventricle. In some embodiments, LV CS lead 52 could bear LA CS pace/sense electrodes 57 and 58 more proximally along the lead body 56 for positioning in operative relation to the LA. Pacing and sensing in the atria may occur using a unipolar or bipolar pair employing one or both of LA CS pace/sense electrodes 57 and 58.

The electrodes designated above as "pace/sense" electrodes can generally be used for both pacing and sensing functions. These "pace/sense" electrodes can be selected to be used exclusively as pace or sense electrodes or to be used for both pacing and sensing in programmed combinations for sensing cardiac signals and delivering cardiac stimulation pulses along selected sensing and pacing vectors. Separate or shared indifferent pace and sense electrodes can also be designated in pacing and sensing functions.

In some embodiments lead 52 may be employed to stimulate the AV node parasympathetic nerves by providing lead 52 with two electrodes located within the coronary sinus, adjacent the ostium. In this location, stimulus pulses are unlikely to trigger depolarizations of the ventricle, but may trigger depolarizations of the atrium, so atrial synchronized stimulation, i.e. during the atrial refractory period, is employed. AV nodal parasympathetic nerve stimulation may also be accomplished by one electrode located adjacent the ostium of the coronary sinus and a second electrode located in the inferior vena cava or by electrodes located in the left atrium or by epicardial electrodes applied on or adjacent the AV nodal fat pad. The most effective electrode location and the tendency to cause depolarization of heart chambers may vary from patient to patient, and may be determined empirically. In some embodiments, a lead employed for stimulating the AV node nerves may be a dedicated lead, provided separately from leads carrying other pace/sense electrodes.

Figure 2:
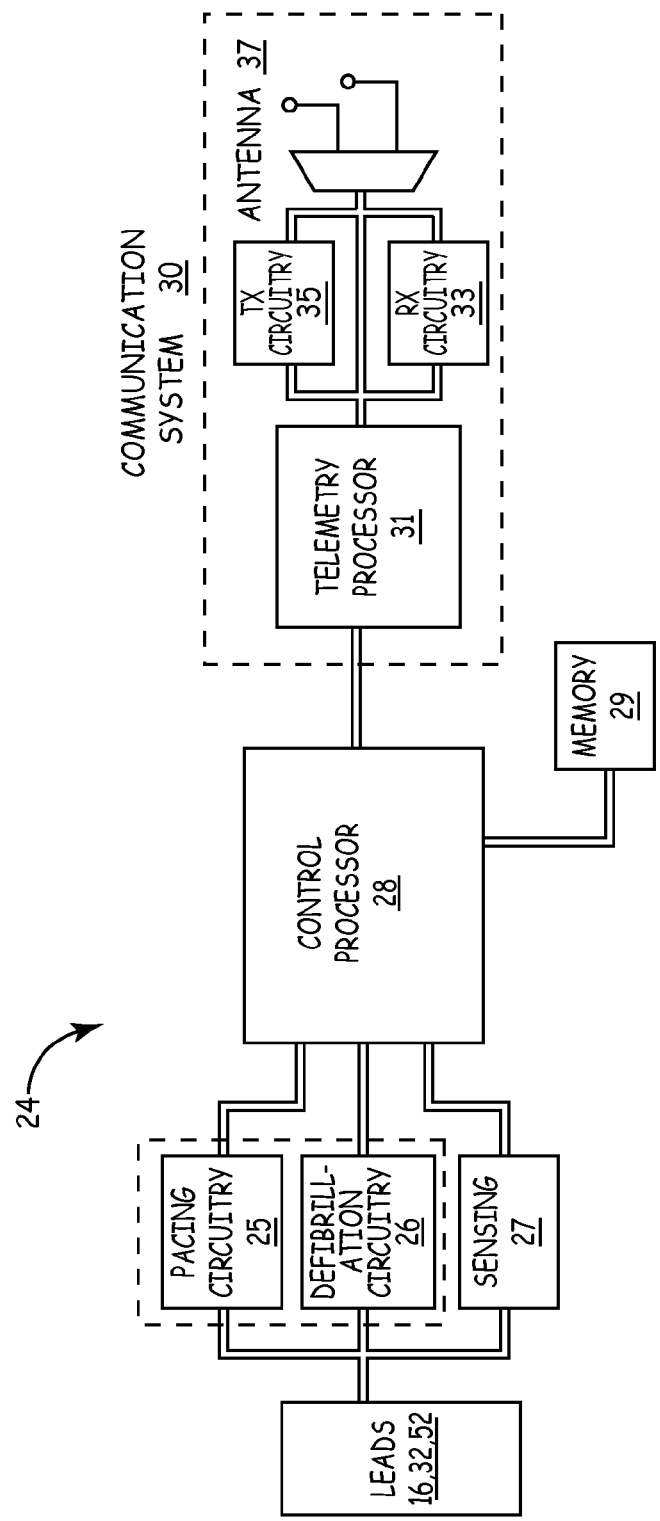
FIG. 2 is a functional block diagram of the IMD shown in FIG. 1, according to one embodiment.

FIG. 2 is a functional block diagram of IMD 14 shown in FIG. 1, according to one embodiment. Circuitry 24, located within IMD 14 of FIG. 1, includes pacing circuitry 25, defibrillation circuitry 26, sensing circuitry 27, control processor 28, memory 29, and communication system 30. Leads 16, 32 and 52 are connected to pacing circuitry 25, defibrillation circuitry 26 and sensing circuitry 27. Each lead (and in turn individual electrodes associated with each lead) coupled to the IMD may be used in multiple capacities to sense cardiac depolarizations (e.g. P-waves and R-waves), deliver AV node stimulation pulses, deliver cardiac pacing pulses, and deliver cardioversion/defibrillation shocks.

Control processor 28 receives input through sensing circuitry 27 from leads 16, 32 and 52 concerning depolarizations sensed by the electrodes connected to leads 16, 32 and 52. Based on input received from sensing circuitry 27, control processor 28 controls cardiac stimulation therapies as needed. Therapy may include providing bradycardia pacing, anti-tachycardia pacing, AV nodal stimulation in combination with ventricular pacing for treating diastolic HF, and other cardiac stimulation therapies requiring low voltage stimulation pulses using pacing circuitry 25 and selected low voltage pace electrodes. Delivered therapy may further include providing defibrillation or cardioversion shocks using defibrillation circuitry 26 and at least one high voltage coil electrode.

Control processor 28 stores selected data relating to cardiac function to memory 29, and retrieves stored data from memory 29 as necessary in performing detection and therapy delivery algorithms. Communication system 30 includes telemetry processor 31, transmission circuitry 35, receiving circuitry 33, and antenna 37. Communication system 30 allows communication between IMD 14 and devices external to the patient for programming IMD 14 and retrieving data stored by IMD 14.

Figure 3:
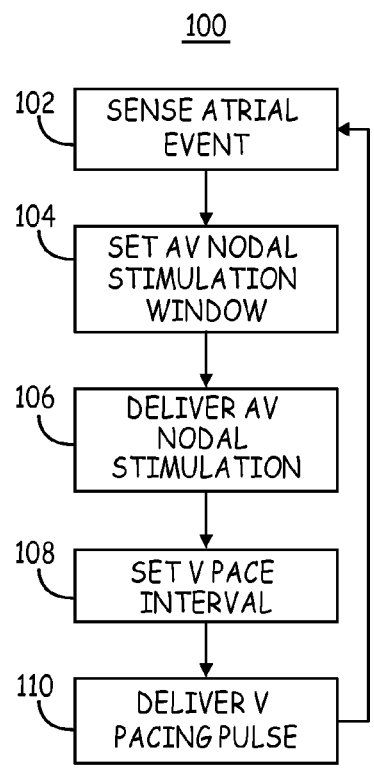
FIG. 3 is a flow chart of a method for controlling a cardiac stimulation therapy.

FIG. 3 is a flow chart 100 of a method performed by IMD 14 for controlling cardiac stimulation. Flow chart 100 and other flow charts presented herein are intended to illustrate the functional operation of the device, and should not be construed as reflective of a specific form of software or hardware necessary to practice the methods described. It is believed that the particular form of software, hardware or firmware will be determined by the particular system architecture employed in the device and by the particular sensing, detection and therapy delivery methodologies employed by the device. Providing software to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 102 sensing circuitry 27 of IMD 14 senses an intrinsic atrial event, i.e. a P-wave, using sensing electrodes located in or on the atria. Control processor 38 is configured to control pacing circuitry 25 to deliver AV nodal stimulation pulses to electrodes associated with lead 16 and/or 52 at defined time intervals during an atrial refractory period. Accordingly, an AV nodal stimulation window is scheduled at block 104 to follow a sensed intrinsic atrial depolarization. A atrial depolarization signal typically conducts across the atria in approximately 60-90 ms. The atrial refractory period is typically approximately 150 ms long. Accordingly an AV nodal stimulation window may be set to begin within approximately 50 to 100 ms following an atrial sensed event and may extend for a duration of approximately 50 to 100 ms, during the atrial refractory period. The AV nodal stimulation window may be selected based on clinical measurements from a population of patients or tailored to an individual patient based on measured P-wave signal width, atrial refractory time measurements, AV conduction time measurements (i.e., PR interval measurements), or any combination thereof.

At block 106, AV nodal stimulation is delivered during the stimulation window. At least one stimulation pulse and typically a train of two or more pulses are delivered during the AV nodal stimulation window. In one embodiment, a 50 Hz pulse train is delivered for the duration of the AV nodal stimulation window. The frequency, amplitude and/or number of AV nodal stimulation pulses may be varied to control the effect of slowing conduction through the AV node. Excessive stimulation of the AV node could lead to AV block. In at least some embodiments, the AV nodal stimulation is intended to prolong the conduction of an intrinsic atrial depolarization to the ventricular chambers to extend or lengthen the PR interval, allowing one ventricle to be paced earlier than the other ventricle.

In an alternative embodiment, AV nodal stimulation is delivered to induce AV block. In this case, atrial and ventricular chamber pacing is delivered with ventricular pacing controlled as described below relative to an atrial pacing pulse (instead of an intrinsic atrial sensed event) to produce ventricular dyssynchrony. Ventricular pacing may be delivered in one or both ventricular chambers in order to maximize ventricular dyssynchrony as will be further described below.

Control processor 38 is further configured to control pacing circuitry 25 to deliver a ventricular pacing pulse to at least one ventricular chamber at a time interval following the onset of the AV nodal stimulation window (or relative to an initiating atrial sensed event) to cause ventricular contraction of the paced ventricle earlier than the depolarization of the other ventricle. The ventricular pacing pulse is scheduled to occur during the prolonged PR interval. A ventricular pacing pulse interval (V pace interval) is set at block 108 so that it will expire prior to the end of the prolonged PR interval.

A ventricular (V) pacing pulse is delivered at block 110 at the expiration of the V pace interval. The ventricular pacing pulse may be timed to coincide substantially with the end of the atrial ejection phase (or somewhat earlier) to preserve the atrial contribution to ventricular filling but prior to intrinsic conduction of the delayed depolarization signal through the AV node. The V pace interval may be set based on clinical measurements or determined individually for a patient based on measured PR intervals during AV nodal stimulation.

The second, non-paced ventricle will be depolarized by either the ventricular pacing pulse being conducted from the first paced ventricle to the second ventricle, by the delayed intrinsic depolarization being conducted through the AV node, or possibly a combination of both. The paced ventricle will be in refractory by the time the delayed depolarization is conducted through the AV node. By pacing one ventricle while delaying intrinsic conduction through the AV node, the paced ventricle will be given a "head start" over the non-paced ventricle in the cardiac cycle. In other words, the paced ventricle will "lead" the second ventricle in the ejection and filling phases of the cardiac cycle. By giving the paced ventricle an early "lead" in diastolic filling, the competitive effect between the two ventricles for the pericardial volume during ventricular diastole is lessened.

The dyssynchrony between the left and right ventricle is maximized to allow filling of one ventricle to begin earlier than the second ventricle to improve impaired filling of the first ventricle associated with DHF. In one embodiment, the cardiac stimulation therapy is delivered to support diastolic impairment of the left ventricle by pacing the left ventricle prior to expiration of a prolonged PR interval to cause earlier ejection and filling of the LV than the RV. In this way, earlier filling of the LV reduces the negative effect of RV filling and competition for the pericardial volume on LV diastolic function.

The cardiac stimulation therapy method shown in FIG. 3 may be delivered continuously, i.e. beat-by-beat, by returning to block 102 after each ventricular pacing pulse. In alternative embodiments, the cardiac stimulation therapy may be delivered periodically during scheduled intervals of time or when the IMD determines a need for therapy, e.g. in response to another physiological sensor such as an activity sensor or a sensor of cardiac hemodynamics.

Figure 4:
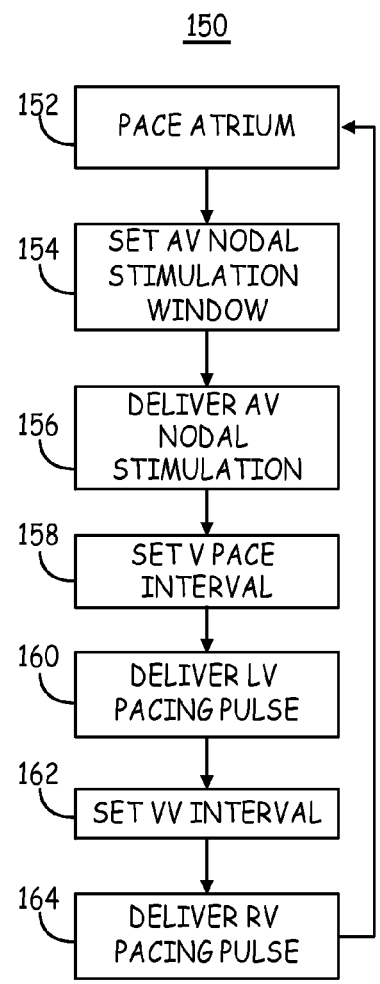
FIG. 4 is a flow chart of an alternative method for delivering a cardiac stimulation therapy.

FIG. 4 is a flow chart 150 of an alternative method for delivering a cardiac stimulation therapy. At block 152, an atrial pacing pulse is delivered in at least one atrial chamber. Atrial pacing may be delivered to control a base heart rate or for facilitating timing of an AV nodal stimulation window. During atrial pacing, the timing of an AV nodal stimulation window may be more predictable and reliable than during atrial sensing since during an intrinsic rhythm heart rate variation may result in variable timing of the stimulation window. P-wave undersensing or P-wave oversensing may occur at times resulting in either missed cardiac cycles or stimulation during non-refractory periods. As such, in some patients it may be desirable to pace the atria for controlling timing and delivery of AV nodal stimulation. Atrial pacing pulses delivered at block 152 are delivered to the atrial myocardium to cause atrial depolarization, rather than being delivered to the specialized AV nodal tissue or AV node parasympathetic nerves.

At block 154, the AV nodal stimulation window is scheduled relative to an atrial pacing pulse to allow delivery of AV nodal stimulation at block 156 during the atrial refractory period following an evoked response to the atrial pacing pulse. At block 158, a V pace interval is set. Upon expiration of the V pace interval, a ventricular pacing pulse is delivered in a first ventricular chamber at block 160, e.g. in the LV, prior to the end of a PR interval prolonged due to the AV nodal stimulation.

At block 162, an inter-ventricular pacing interval (VV interval) may be set to enable pacing of the second ventricle, e.g. the RV, at block 164. Upon expiration of the predetermined VV interval following the first V pace delivered at block 160, a V pace pulse is delivered in the second ventricle. The VV interval may be set to control the degree of ventricular dyssynchrony while allowing the LV to lead the RV in the diastolic filling phase. Depending on the degree of slowing of AV nodal conduction, an intrinsically conducted depolarization may arrive at the RV causing RV depolarization prior to an RV pacing pulse delivered at a predetermined VV interval.

In other embodiments, the RV may be paced upon expiration of a programmed AV interval (set at block 162 instead of a VV interval). Following the atrial pacing pulse delivered at block 152, the AV interval is started and an RV pacing pulse is delivered at block 164 upon expiration of the AV interval (if an intrinsic RV R-wave is not sensed first). In this case, the AV interval would be set to an interval expiring later than delivery of the LV pacing pulse and during the LV refractory period, allowing LV filling to lead RV filling.

Figure 5:
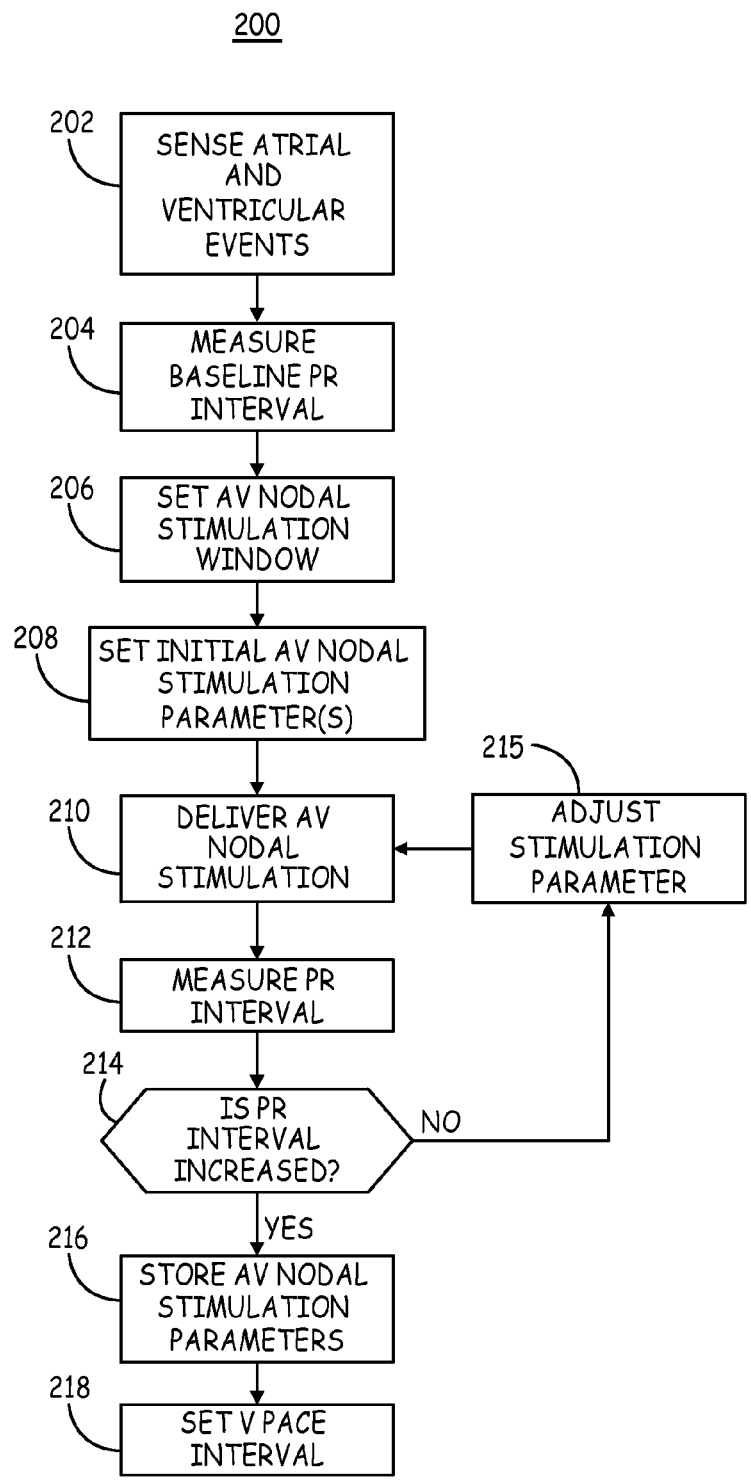
FIG. 5 is a flow chart of one method for adjusting cardiac stimulation control parameters according to one embodiment.

FIG. 5 is a flow chart 200 of a method for adjusting cardiac stimulation parameters used to control a therapy according to one embodiment. At block 202, atrial and ventricular signals, i.e. P-waves and R-waves, are sensed. PR intervals are measured at block 204 to determine a baseline PR interval as a measure of the AV conduction time when no therapy is being delivered. One or more PR intervals may be measured with an average or median measurement taken as a baseline PR interval measurement.

At block 206, an AV nodal stimulation window is set to occur substantially within an atrial refractory period. Initial AV nodal stimulation parameters are set at block 208 for controlling stimulation pulses during the AV nodal stimulation window. In one embodiment, a default pulse amplitude, pulse frequency and pulse number are selected. In other embodiments, the pulse number is controlled by setting the pulse frequency and the duration of the AV nodal stimulation window to fill the window with a pulse train having the programmed frequency.

At block 210, AV nodal stimulation is delivered during the stimulation window according to the initial control parameters. The PR interval is measured again at block 212. The PR interval is compared to the baseline PR interval at decision block 214 to determine if the PR interval is increased in response to the AV nodal stimulation. If the PR interval is not increased compared to the baseline PR interval, or not increased by at least some threshold amount for enabling early pacing of one of the ventricular chambers relative to the other ventricular chamber, one or more control parameters is adjusted at block 215. The amplitude, frequency or number of pulses may be increased to slow AV node conduction and prolong the PR interval.

Once the PR interval is satisfactorily increased (decision block 214), the AV nodal stimulation parameters are stored at block 216. These parameters will be used for AV nodal stimulation during delivery of the cardiac stimulation therapy.

At block 218, a ventricular pace interval is set for delivering a pacing pulse to a first ventricular chamber. The V pace interval is set to cause a pacing pulse delivered to the first ventricular chamber to occur prior to the end of the prolonged PR interval such that the first ventricular chamber will be in refractory by the end of the PR interval. At the end of the PR interval, the second ventricular chamber will be depolarized by the delayed depolarization signal conducted through the AV node. The V pace interval may be set at block 218 as a time interval beginning at a sensed P-wave and ending prior to the end of the prolonged PR interval measured at block 212.

The method shown in FIG. 5 may be performed during both atrial sensing and atrial pacing to obtain different sets of optimal settings for the AV nodal stimulation and V pacing during atrial sensing and during atrial pacing. Since conduction of an atrial pacing pulse may result in somewhat different conduction times through the heart and relative timing of associated refractory periods than an intrinsic atrial depolarization, the optimal AV nodal stimulation parameters, stimulation window and V pace interval may be different when the atria are paced compared to during intrinsic atrial activation.

As such, the method depicted in flow chart 200 may additionally be performed during atrial pacing at block 202 in place of atrial sensing with measured AR intervals indicating the time interval between an atrial pacing pulse and a sensed R-wave at block 204. The AV nodal stimulation parameters would be adjusted until the AR interval is lengthened a satisfactory amount. An AV pacing interval may then be set at block 218 to time delivering of the ventricular pacing pulse following an atrial pacing pulse, within the prolonged AR interval.

It is further recognized that the optimal AV nodal stimulation window, AV nodal stimulation parameters and V pace interval may change with heart rate. As such, different stimulation parameters and V pace intervals may be stored for different heart rates or heart rate ranges, which may be paced or sensed heart rates. Heart rate dependent therapy delivery control parameters may be determined and stored by performing the method shown in FIG. 5 during different rates of sensed (or paced) atrial events. During therapy delivery, the stimulation parameters and V pace intervals applied may be selected based on whether an initiating atrial event is a paced or sensed event and what the currently measured heart rate is.

The therapy control parameters may be re-evaluated periodically (e.g., every 1 minute, 2 minutes, 5 minutes or other scheduled interval) or in response to changes in a heart rate, which may be an intrinsic rate or a paced rate, e.g. in response to changes in an activity sensor indicated pacing rate. During therapy delivery, sensing of atrial events may include atrial rate monitoring (paced or sensed) for several successive cardiac cycles to confirm a change in heart rate and timing intervals (AV nodal stimulation window and V pace interval) may then be adjusted to control the stimulation therapy as needed with changes in heart rate.

Figure 6:
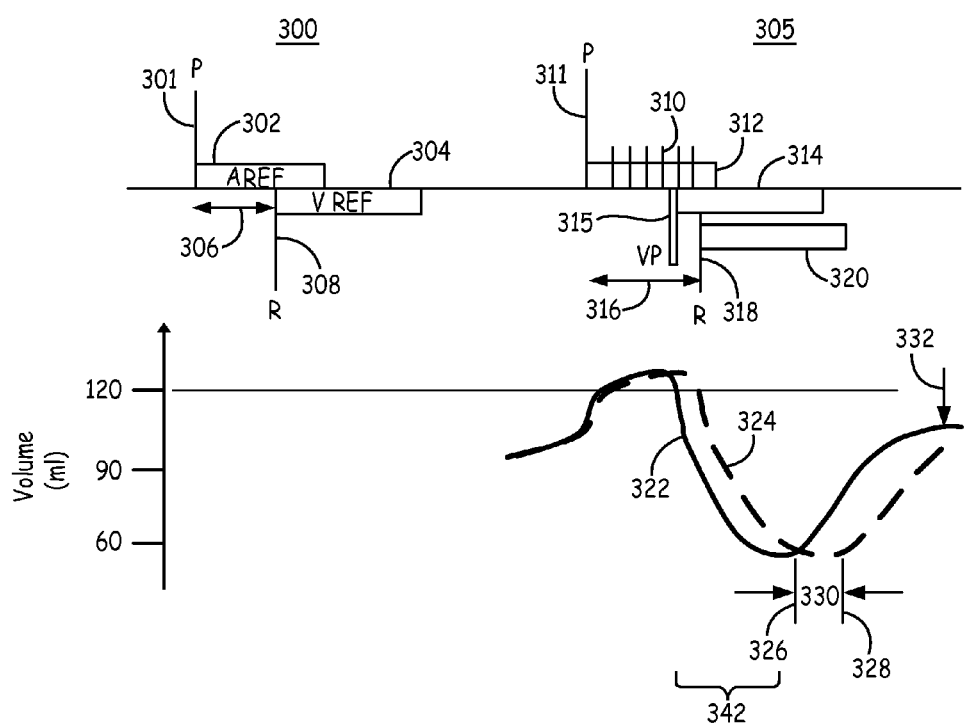
FIG. 6 is a timing diagram depicting the temporal relationship of cardiac events during a cardiac stimulation therapy according to one embodiment.

FIG. 6 is a timing diagram 300 depicting the temporal relationship of cardiac events during a cardiac stimulation therapy for treating DHF according to one embodiment. Prior to starting the cardiac stimulation therapy, during cardiac cycle 300, an atrial P-wave 301 is sensed. P-wave 301 is followed by an atrial refractory period 302. The P-wave 301 is conducted to the ventricles to cause a ventricular depolarization and sensed R-wave 308. The P-wave 301 and the R-wave 308 are separated by a PR interval 306. The R-wave is followed by a ventricular refractory period 304. The R-wave 308 in this intrinsic heart beat corresponds to the synchronized depolarization of the RV and LV.

On cardiac cycle 305, stimulation therapy is delivered. The sensed P-wave 311 is followed by AV nodal stimulation pulses 310 during the atrial refractory period 312. The AV nodal stimulation pulses 310 cause a prolongation of the PR interval 316. During the PR interval 316, a ventricular pacing pulse 315 is delivered in one ventricular chamber, e.g. the LV, to promote dyssynchrony between the left and right ventricles. The V pacing pulse 315 is followed by a ventricular refractory period 314 in the paced ventricle.

At the end of the PR interval 316, the second ventricle, e.g. the RV, is depolarized by the atrial depolarization signal conducted through the AV node. The depolarization of the second ventricle is represented by R-wave 318, which corresponds to the depolarization of only the second ventricle. The first, paced ventricle remains in refractory 314 at the end of the prolonged PR interval 316 and is not depolarized by the intrinsically conducted depolarization signal. A ventricular refractory period 320 follows the R-wave 318 in the second ventricle.

The cardiac stimulation therapy which includes AV nodal stimulation pulses 310 and an early, single-chamber V pacing pulse 315 increases dysynchrony between the ventricles such that the paced ventricle will lead the non-paced ventricle in ejection and filling. The therapy may optionally include atrial pacing pulses and bi-ventricuar pacing as described above.

If the LV is the first paced ventricle and the RV is the second ventricle, the dyssynchronous volume changes of the LV and RV over the cardiac cycle can be observed as shown in FIG. 6. An LV volume curve 322 is shown to lead an RV volume curve 324 during the ejection phase 342. As a result, LV filling onset 326 begins a time interval 330 earlier than the onset 328 of RV filling. At the end of the passive filling phase 322, the LV volume (curve 322) has "caught up" with the RV volume (curve 324). A subsequent active filling phase will occur with atrial activation.

Figure 7:
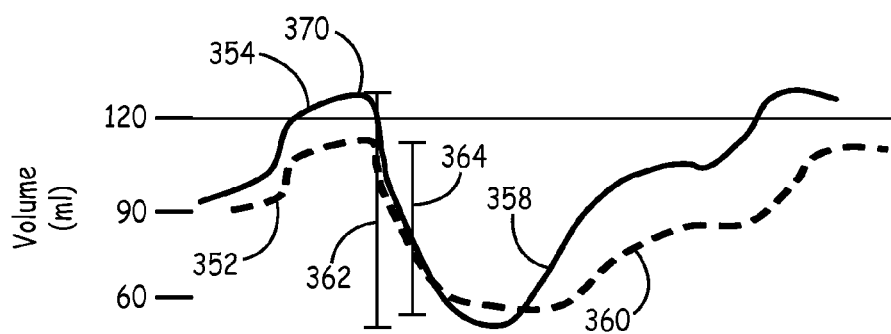
FIG. 7 is a graphical depiction of representative LV volume curves before and during the cardiac stimulation therapy.

FIG. 7 is a depiction of representative LV volume curves before and during the cardiac stimulation therapy. The curves 352 and 354 are shown to illustrate the expected effects of the cardiac stimulation therapy and may be somewhat exaggerated to show these effects and not drawn exactly to scale. Volume curve 352 corresponds to no therapy delivery. LV stiffness and competition for the pericardial volume limits passive filling of the LV as observed by the diminished positive slope during the passive filling phase at 360. When the cardiac stimulation therapy is delivered, including AV nodal stimulation and early LV pacing relative to RV depolarization, passive filling indicated at 358 is improved (steeper) because LV filling leads RV filling (not shown). This earlier filling results in an increased end-diastolic volume 370 and thus improves LV stroke volume 362 as compared to stroke volume 364 before therapy.

Thus, an implantable medical device and associated cardiac stimulation method have been presented in the foregoing description with reference to specific embodiments. It is appreciated that various modifications to the referenced embodiments may be made without departing from the scope of the disclosure as set forth in the following claims.

The invention claimed is:

1. A medical device for stimulating a patient's heart, comprising:
a plurality of electrodes;
pacing circuitry coupled to the plurality of electrodes to deliver, via the plurality of electrodes, an atrial pacing pulse to an atrial chamber to generate an evoked atrial depolarization and to deliver a stimulation pulse to an atrioventricular node of the heart; and
a processor coupled to the pacing circuitry, the processor configured to deliver the stimulation pulse to increase a PR interval of the heart by delivering the stimulation pulse during a stimulation window having a start time corresponding to the delivered atrial pacing pulse so that the stimulation pulse is delivered during a refractory period corresponding to the evoked atrial depolarization, and to deliver a ventricular pacing pulse to a first ventricular chamber during the increased PR interval to cause a contraction of the first ventricular chamber to occur prior to a contraction of a second ventricular chamber to increase dyssynchrony between the contraction of the first ventricular chamber and the contraction of the second ventricular chamber.

2. The device of claim 1, wherein the processor is further configured to determine whether the increase in the PR interval is greater than a predetermined threshold, and adjust the stimulation pulse in response to the determining.

3. The device of claim 2, wherein adjusting the stimulation pulse comprises increasing one of an amplitude of the stimulation pulse and a frequency of the stimulation pulse.

4. The device of claim 1, wherein the processor is further configured to deliver a ventricular pacing pulse to the second ventricular chamber during a refractory period of the first ventricular chamber, the refractory period corresponding to the ventricular pacing pulse delivered to the first ventricular chamber.

5. The device of claim 4, wherein the processor is further configured to determine whether an inter-ventricular interval following delivery of the ventricular pacing pulse to the first ventricular chamber has expired, and deliver the ventricular pacing pulse to the second ventricular chamber in response to the inter-ventricular interval being expired.

6. The device of claim 1, wherein the processor is further configured to sense sensing intrinsic atrial events, generate first parameters associated with at least one of the stimulation pulse and the ventricular pacing pulse in response to atrial pacing pulses, and generate second parameters associated with at least one of the stimulation pulse and the ventricular pacing pulse in response to the sensed intrinsic atrial events, wherein the stimulation pulse and the ventricular pacing pulse are delivered using the first generated parameters in response to delivery of atrial pacing and using the second parameters in response to intrinsic atrial activation.

7. The device of claim 6, wherein the first parameters and the second parameters comprise one of an electrical pulse amplitude, a pulse frequency, and a number of electrical pulses.

8. The device of claim 1, wherein the processor is further configured to determine a plurality of first heart rate parameters corresponding to different rates of paced atrial events to generate corresponding pacing heart rate parameters, determine a plurality of second heart rate parameters corresponding to different rates of sensed atrial events to generate corresponding sensing heart rate parameters, and determine a current heart rate, wherein the stimulation pulse and the ventricular pacing pulse are delivered using a pacing heart rate parameter of the generated pacing heart rate parameters corresponding to the determined heart rate in response to a paced atrial event, and using a sensing heart rate parameter first heart rate dependent therapy delivery control parameters corresponding to the determined heart rate in response to a sensed atrial event.

9. The device of claim 1, wherein the first ventricular chamber corresponds to a left ventricle and the second ventricular chamber corresponds to a right ventricle.

10. A method for stimulating a patient's heart, comprising:
delivering an atrial pacing pulse to an atrial chamber to generate an evoked atrial depolarization;
delivering a stimulation pulse to an atrioventricular node to increase a PR interval of the heart by delivering the stimulation pulse during a stimulation window having a start time corresponding to the delivered atrial pacing pulse so that the stimulation pulse is delivered during a refractory period corresponding to the evoked atrial depolarization; and
delivering a ventricular pacing pulse to a first ventricular chamber during the increased PR interval to cause a contraction of the first ventricular chamber to occur prior to a contraction of a second ventricular chamber to increase dyssynchrony between the contraction of the first ventricular chamber and the contraction of the second ventricular chamber.

11. The method of claim 10, further comprising:
determining whether the increase in the PR interval is greater than a predetermined threshold; and
adjusting the stimulation pulse in response to the determining.

12. The method of claim 11, wherein adjusting the stimulation pulse comprises increasing one of an amplitude of the stimulation pulse and a frequency of the stimulation pulse.

13. The method of claim 10, further comprising delivering a ventricular pacing pulse to the second ventricular chamber during a refractory period of the first ventricular chamber, the refractory period corresponding to the ventricular pacing pulse delivered to the first ventricular chamber.

14. The method of claim 13, further comprising:
determining whether an inter-ventricular interval following delivery of the ventricular pacing pulse to the first ventricular chamber has expired; and
delivering the ventricular pacing pulse to the second ventricular chamber in response to the inter-ventricular interval being expired.

15. The method of claim 10, further comprising:
sensing intrinsic atrial events;
generating first parameters associated with at least one of the stimulation pulse and the ventricular pacing pulse in response to atrial pacing pulses; and
generating second parameters associated with at least one of the stimulation pulse and the ventricular pacing pulse in response to the sensed intrinsic atrial events, wherein the stimulation pulse and the ventricular pacing pulse are delivered using the first generated parameters in response to delivery of atrial pacing and using the second parameters in response to intrinsic atrial activation.

16. The method of claim 15, wherein the first parameters and the second parameters comprise one of an electrical pulse amplitude, a pulse frequency, and a number of electrical pulses.

17. The method of claim 10, further comprising:
determining a plurality of first heart rate parameters corresponding to different rates of paced atrial events to generate corresponding pacing heart rate parameters;
determining a plurality of second heart rate parameters corresponding to different rates of sensed atrial events to generate corresponding sensing heart rate parameters; and
determining a current heart rate, wherein the stimulation pulse and the ventricular pacing pulse are delivered using a pacing heart rate parameter of the generated pacing heart rate parameters corresponding to the determined heart rate in response to a paced atrial event, and using a sensing heart rate parameter first heart rate dependent therapy delivery control parameters corresponding to the determined heart rate in response to a sensed atrial event.

18. The method of claim 10, wherein the first ventricular chamber corresponds to a left ventricle and the second ventricular chamber corresponds to a right ventricle.

19. A non-transitory computer readable medium having computer executable instructions for performing a method for stimulating a patient's heart, comprising:
delivering an atrial pacing pulse to an atrial chamber to generate an evoked atrial depolarization;
delivering a stimulation pulse to an atrioventricular node to increase a PR interval of the heart by delivering the stimulation pulse during a stimulation window having a start time corresponding to the delivered atrial pacing pulse so that the stimulation pulse is delivered during a refractory period corresponding to the evoked atrial depolarization; and
delivering a ventricular pacing pulse to a first ventricular chamber during the increased PR interval to cause a contraction of the first ventricular chamber to occur prior to a contraction of a second ventricular chamber to increase dyssynchrony between the contraction of the first ventricular chamber and the contraction of the second ventricular chamber.

20. A medical device for stimulating a patient's heart, comprising:
a plurality of electrodes;
pacing circuitry coupled to the plurality of electrodes to deliver, via the plurality of electrodes, an atrial pacing pulse to an atrial chamber to generate an evoked atrial depolarization and to deliver stimulation to an atrioventricular node of the heart; and
a processor coupled to the pacing circuitry, the processor configured to deliver the stimulation to the atrioventricular node to increase a PR interval of the heart, the stimulation delivered during a stimulation window and comprising a train of at least two pulses that cause prolonged conduction of the evoked atrial depolarization to a ventricular chamber, and to deliver a ventricular pacing pulse to a first ventricular chamber during the increased PR interval to cause a contraction of the first ventricular chamber to occur prior to a contraction of a second ventricular chamber to increase dyssynchrony between the contraction of the first ventricular chamber and the contraction of the second ventricular chamber.

* * * * *